United States Patent
Jinno et al.

(10) Patent No.: US 7,544,836 B2
(45) Date of Patent: Jun. 9, 2009

(54) PROCESS FOR PRODUCING (METH)ACROLEIN OR (METH)ACRYLIC ACID

(75) Inventors: Kimikatsu Jinno, Mie (JP); Yasushi Ogawa, Mie (JP); Yoshiro Suzuki, Mie (JP); Shuhei Yada, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 283 days.

(21) Appl. No.: 11/596,287

(22) PCT Filed: Oct. 25, 2004

(86) PCT No.: PCT/JP2004/016171

§ 371 (c)(1),
(2), (4) Date: Mar. 23, 2007

(87) PCT Pub. No.: WO2005/110956

PCT Pub. Date: Nov. 24, 2005

(65) Prior Publication Data
US 2008/0045748 A1 Feb. 21, 2008

(30) Foreign Application Priority Data
May 13, 2004 (JP) ............................. 2004-143305

(51) Int. Cl.
C07C 51/16 (2006.01)
C07C 51/235 (2006.01)
(52) U.S. Cl. ...................... 562/545; 562/532
(58) Field of Classification Search ............... 562/545, 562/532
See application file for complete search history.

(56) References Cited

U.S. PATENT DOCUMENTS 4,873,368 A 10/1989 Kadowaki et al.
5,276,178 A * 1/1994 Onodera et al. ............. 562/537

FOREIGN PATENT DOCUMENTS

| JP | 49 132007 | 12/1974 |
| JP | 62-17579 | 4/1987 |
| JP | 5 125010 | 5/1993 |
| JP | 8 266862 | 10/1996 |

OTHER PUBLICATIONS

U.S. Appl. No. 11/596,287, filed Nov. 13, 2006, Jinno, et al.
U.S. Appl. No. 11/597,365, filed Nov. 22, 2006, Ogawa, et al.
U.S. Appl. No. 11/587,990, filed Oct. 30, 2006, Jinno, et al.
U.S. Appl. No. 11/451,355, filed Jun. 13, 2006, Yada, et al.
U.S. Appl. No. 11/596,366, filed Nov. 14, 2006, Ogawa, et al.
U.S. Appl. No. 11/597,276, filed Nov. 20, 2006, Yada, et al.

* cited by examiner

Primary Examiner—D. Margaret Seaman
Assistant Examiner—Nizal S Chandrakumar
(74) Attorney, Agent, or Firm—Oblon, Spivak, McClelland, Maier & Neustadt, P.C.

(57) ABSTRACT

An object of the invention is to provide a production method for (meth)acrolein or (meth)acrylic acid which can continue an operation without causing a decomposition reaction of acrolein or the like.

According to the invention, provided is a production method for (meth)acrolein or (meth)acrylic acid, in which (meth)acrolein or (meth) acrylic acid is obtained by performing a catalytic gas phase oxidation on propylene, propane or isobutylene by using oxygen by means of a heat-exchange type multi-tubular reactor, having a tube bundle portion in which a multiple of reaction tubes each filled with a catalyst are aligned in parallel to one another and a tube plate which is adjacent to a downstream side of the tube bundle portion of the reaction tubes and forms a lead-out portion for a reaction gas, in which the tube bundle portion of the reaction tubes has a hollow-columnar constitution as a whole, and which is characterized in that a rectifier is provided on a tube plate.

4 Claims, 1 Drawing Sheet

PROCESS FOR PRODUCING (METH)ACROLEIN OR (METH)ACRYLIC ACID

TECHNICAL FIELD

The present invention relates to a production method for (meth)acrolein or (meth)acrylic acid and, particularly, to a method for producing (meth)acrolein or (meth)acrylic acid in a safe economical manner by preventing a gas containing (meth)acrolein from being retained in a space in an outlet side of a reaction tube.

The term "(meth)acrolein" as used herein means "acrolein or methacrolein", and the term "(meth)acrylic acid" as used herein means "acrylic acid or methacrylic acid".

BACKGROUND ART (Meth)acrylic acid or (meth)acrolein has ordinarily been produced in a continuous manner by performing a gas-phase catalytic oxidation reaction on propylene, propane, isobutylene or (meth)acrolein by using molecular oxygen or a gas containing molecular oxygen in the presence of a complex oxide catalyst by means of a multi-tube type reactor having a plurality of reaction tubes each filled with a catalyst.

Since a retention portion, in which reaction tubes are not present, in a lead-out portion for a reaction gas in an outlet side of the multi-tube type reactor to be used in this method holds, although depending on specifications of the reactor, from 5 to 20% of an outer diameter of a reaction tube bundle, a volume of the retention portion has a size which can not be neglected compared with a flow volume of the reaction gas.

As a result, a problem is caused such that a reaction product in the reaction gas is decomposed in the retention portion to produce a by-product which, then, decreases a purity of (meth)acrylic acid or (meth)acrolein to be targeted or is changed into be a heavy by-product which, then, prevents the catalytic gas phase oxidation process from being continued or the like.

In Patent Document 1 (JP-A-5-125010), it is proposed that, by allowing a volume of the lead-out portion of the reaction gas in the outlet side of an oxidation reaction tube to be smaller than that of a lead-in portion for a raw material gas, a retention period of time in the lead-out portion for the reaction gas in the reaction tube outlet side, the retention period of time in the lead-out portion in the reaction tube outlet side is allowed to be short and, then, production of diketones as by-products is suppressed.

In Patent Document 2 (JP-B-62-17579), it is proposed that, in a downstream side adjacent to a catalyst layer in a reaction band region, a cooling portion comprising a filling layer of a solid inert material is provided. However, when the reaction gas is cooled, a heavy impurity having a high boiling point which is present in the gas is condensed to clog the reactor or the like and, then, an operation becomes sometimes incapable of being continuously performed.

DISCLOSURE OF THE INVENTION

An object of the present invention is to provide a production method for (meth)acrolein or (meth)acrylic acid, comprising a step of supplying propylene, propane or isobutylene, and a gas containing a molecular oxygen to a reactor having reaction tubes each filled with a catalyst and performing a catalytic gas phase oxidation to obtain a reaction gas containing (meth)acrylic acid or (meth)acrolein, which prevents a reaction product, particularly, acrolein in a retention portion in an outlet side of the reactor from being decomposed.

According to the present invention, a production method for (meth)acrolein or (meth)acrylic acid, in which (meth)acrolein or (meth) acrylic acid is obtained by performing a catalytic gas phase oxidation reaction on propylene, propane or isobutylene by using a molecular oxygen by means of a heat-exchange type multi-tubular reactor, comprising a tube bundle portion in which a multiple of reaction tubes each filled with a catalyst are aligned in parallel to one another, a tube plate which is adjacent to a downstream side of the tube bundle portion of the reaction tubes and a lead-out portion for a reaction gas under the tube plate, in which the tube bundle portion of the reaction tubes has a hollow columnar constitution as a whole, being characterized in that a rectifier is provided on a tube plate is provided, to thereby achieve the object of the present invention.

According to the method of the present invention, an operation can continuously be performed without causing a decomposition reaction of (meth)acrolein.

Figure 1:
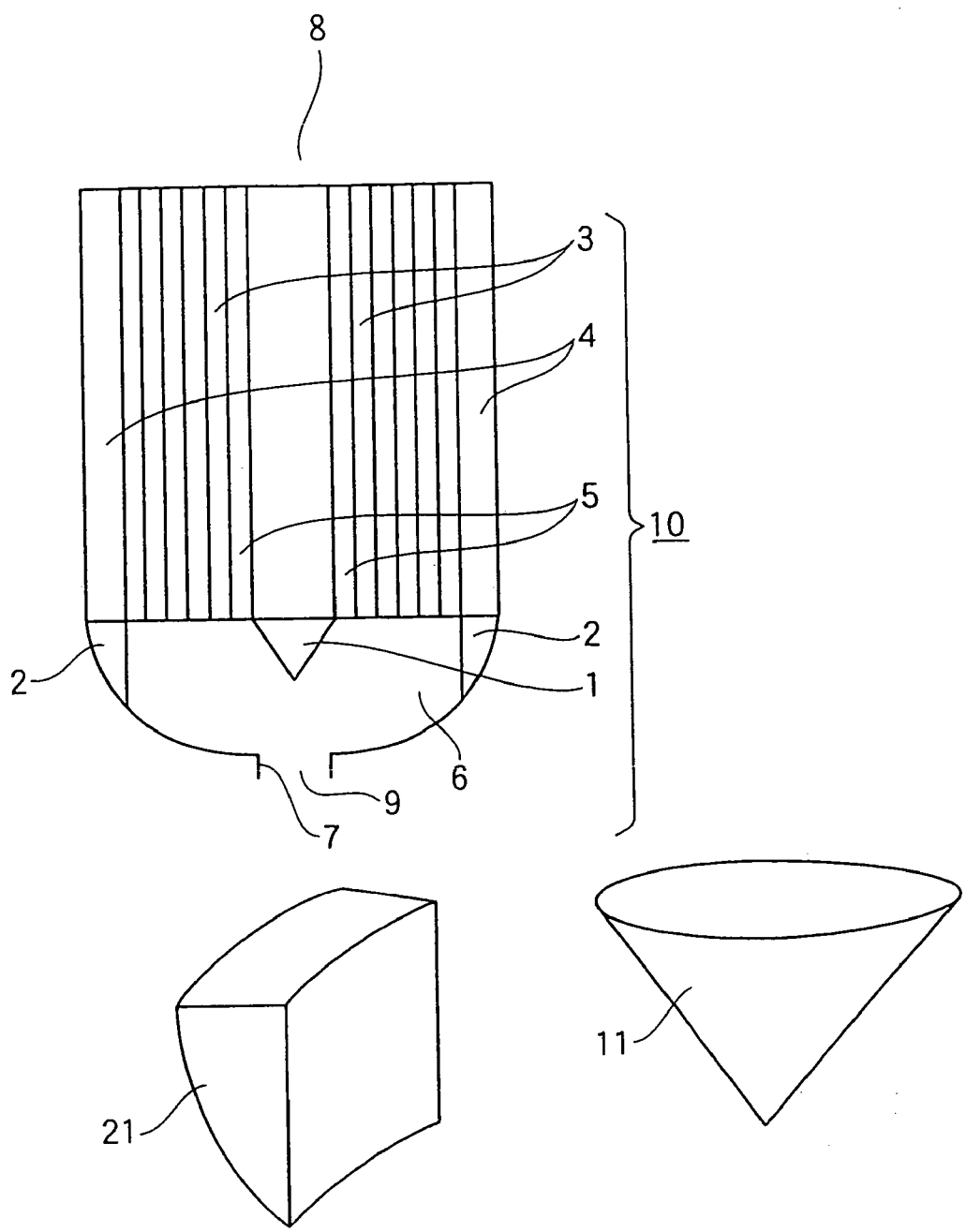
FIG. 1 is a schematic diagram showing an example of a reactor according to the present invention.

As for numerals and marks in FIG. 1, 1 denotes a rectifier 1 in a conical shape; 2 denotes a rectifier 2 in a box shape; 3 denotes a reaction tube bundle; 4 denotes a periphery of the reaction tube bundle; 5 denotes an inner circumference of the reaction tube bundle; 6 denotes a space forming a lead-out portion for a reaction product in an outlet tube plate side of the reaction tube bundle; 7 denotes a lead-out tube for the reaction product provided at a bottom edge of the tube plate; 8 denotes an inlet portion of a multi-tubular reactor; 9 denotes an outlet portion of the reactor; 10 denotes the reactor configured with the aforementioned portions 1 to 9; 11 shows an enlarged perspective diagram of the rectifier 1 in the conical shape; and 21 shows an enlarged perspective diagram of the rectifier 2 in the box shape.

BEST MODE FOR CARRYING OUT THE INVENTION

Hereinafter, the present invention will be described in detail with reference to embodiments of producing acrolein and acrylic acid from propylene.

In production of acrolein and acrylic acid, propylene, an inert gas and air as a molecular oxygen source are mixed thereamong and, then, subjected to a catalytic gas-phase oxidation in the presence of a catalyst.

When acrylic acid is produced, acrolein to be obtained is further subjected to the catalytic gas-phase oxidation, and such reactions can be performed in one reactor. When the reactions are performed in one reactor, a concentration of acrolein at an outlet of the reactor is ordinarily from 4 to 8% by volume.

For the catalytic gas-phase oxidation, a multi-tubular heat-exchange type reactor is used. As far as the knowledge of the present inventors go, it has been found that a gas retention portion is present in a central portion of a tube plate in an outlet side of the reactor in which a reaction tube is absent and, then, it is important to eliminate the retention portion. As previously described, although it has been known to shorten a retention period of time in a region in which the reaction gas is present in the outlet side of the reactor, it is a new knowledge obtained by the present inventors that there is the retention portion and the retention portion causes such a trouble as reduces yield of acrolein.

When a simulation is conducted by using a computer programmed with a decomposition reaction of acrolein, amazingly, heat caused by the decomposition reaction which is generated in the retention portion and is so minute as not give an influence on the yield is gradually accumulated to raise a gas temperature and, then, the thus-accumulated heat further accelerates the decomposition reaction and, finally, leads to such a decomposition reaction as noticeably reduces the yield.

According to the present invention, a rectifier is provided in this portion. As for the rectifier having such a shape as does not retain gas, any rectifier is permissible so long as it protrudes toward a lead-out tube in the downstream of the tube plate in the outlet side of the reactor and a protrusion having an occupied area which becomes smaller from the upstream to the downstream is preferable and, on this occasion, a tip portion is not necessarily sharp.

As for shapes of the rectifier, a conical shape, a polyangular pyramid such as a triangular pyramid or a quadrangular pyramid, or a shape having a round tip end thereof is mentioned.

As for materials for the rectifier, for example, a material which does not react with the reaction gas is preferable. Specifically, a material made of stainless steel such as SUS 304 or SUS 316 is formed in a shape corresponding to that as described above and, then, fixed by welding, using a bolt or the like. When the material is hollow, a care is taken such that the reaction gas does not enter the inside thereof.

As for sizes of the rectifier, although the sizes vary depending upon the reactor and the operation conditions thereof, it is preferable that a maximum area of a cut-section of the rectifier at the time of being cut in a plane is from 50 to 100% of an area of a cut-section of a portion in which the reaction tube is absent of the reactor. The rectifier is adaptable without any problem, so long as length thereof in a direction of the downstream is 20% or more of a diameter of a cut-section of a portion in which the reaction tube is absent of the reactor, and it may have a length up to an inside of the lead-out tube so long as a cross-sectional area of the lead-out tube in the downstream is not smaller by 30% or more.

A position in which the rectifier is provided is not particularly limited, so long as the retention of the gas is eliminated, but the rectifier is preferably provided in a central portion of the tube plate in the outlet side of the reaction tube or a peripheral portion thereof in which the reaction tube is absent.

The rectifier may be formed from a material having a hollow of such as a metallic net shape or a mesh shape.

On this occasion, the retention can be prevented by filling an inside of the hollow of the metallic net, etc. with a filling article.

As for such filling articles, any article is permissible, so long as it is an inert substance, is stable under reaction conditions of generating acrolein/acrylic acid, and has no reactivity with a raw material such as olefin, or a product such as an unsaturated aldehyde or an unsaturated fatty acid.

Specifically, articles as being used as a carrier for a catalyst, such as alumina, silicon carbide, silica, zirconium oxide and titanium oxide are permissible. Further a shape thereof is not particularly limited similarly to the case of the catalyst and any one of a spherical shape, a columnar shape, a ring shape and an indeterminate shape is permissible.

A method for providing any one of these filling articles is not particularly limited and, for example, a container is firstly formed in the aforementioned shape by using the metallic net and, then, the filling article is filled therein, or, in a case in which a formed body has a substantial size, it may individually be seized and fixed by using a wire, a bolt or the like.

In FIG. 1, an example of the reactor according to the present invention in which a gas flow is downward and an outlet of the reactor is present in a lower portion thereof is schematically shown. In FIG. 1, a multi-tubular reactor 10 comprising, in an upper portion thereof, an inlet portion 8 of the multi-tubular reactor (a shape of a top portion being omitted) which introduces a reaction gas into the reactor 10 and, in a lower portion thereof, an outlet 9 of the reactor from which the reaction gas is discharged, in which, inside the reactor 10 in a cylindrical shape, a reaction tube bundle 3 constituted with a multiple of tubes is arranged between the periphery 4 and an inner circumference 5 of the reaction tube bundle in a parallel manner and, further, a cylindrical manner as a whole and, in an outlet side of the tube plate positioned under the tube bundle, a space 6 which receives a reaction product from the reaction tube bundle is formed and, then, the reaction product is let out of the reactor from the space 6 via a lead-out tube 7.

Therefore, the reactor is configured such that the reaction gas is not retained and led out into the outside of the reactor. Further, such configuration does not restrict a direction of a gas flow.

In order to prevent a reaction by-product having a high boiling point from being stuck, the reaction gas is preferably not cooled, but it can appropriately be cooled in combination with a rectifying constitution according to the present invention.

In FIG. 1, in the space 6 under the reaction tube bundle 3, the rectifier 1 which is a conical container (a disk is welded on a bottom portion of a cone) worked from a stainless steel sheet is fixed by welding to a tube plate in the lower side of the reaction tube (refer to FIG. 1, rectifier 1 and enlarged perspective diagram 11 thereof).

In the space 6 under the peripheral side 4 of the reaction tube bundle 3, rectifiers 2 in each of which a box-type container constituted by one curved face (being in a close contact with an inner wall of the reactor) and four flat sheets is fabricated by welding a stainless steel sheet are arranged in all circumferential portions along an inner wall of the reactor 10 and, then, fixed by screws to fixing hooks welded to the inner wall (refer to FIG. 1, rectifier 2 and enlarged perspective diagram 21 thereof).

As for preferable conditions for the reaction gas, at the time of applying the method according to the present invention, a concentration of acrolein in the gas at the outlet of the reactor is preferably from 0.1 to 10% and, more preferably, from 1 to 8%.

When acrylic acid is produced by using two reactors in series, it is preferable to apply the method according to the present invention as a pre-step reactor.

EXAMPLES

Hereinafter, the present invention will be described more particularly with reference to embodiments.

Example 1

In performing an oxidation reaction on propylene, catalyst powder having a composition comprising Mo (12) Bi (5) Ni (3) Co (2) Fe (0.4) Na (0.2) B (0.4) K (0.1) Si (24) O (x) was produced as a catalyst. Numerals in respective parentheses indicate atomic ratios and a composition x of oxygen is a value to be determined in accordance with an oxidation state of each metal. The catalyst powder was molded to form a solid catalyst and, then, used.

Stainless steel-made containers in shapes as shown in FIG. 1 (rectifier 1 and rectifier 2) were provided by using an oxidation reactor with an inner diameter of 4 m having reaction tubes made of stainless steel each having a length of 3.5 m, an inner diameter of 24 mm$\phi$ and an outer diameter of 28 mm$\phi$.

While adjusting an inlet pressure of the reactor to be 75 kPa (gauge pressure), a raw material gas comprising steam of 28% by volume, air of 64% by volume, propylene of 8% by volume was supplied. A concentration of acrolein at an outlet portion of the reactor was 6.5% by volume.

Although an operation was continuously performed for 6 months, the operation was conducted in a consistent manner without causing decomposition of an acrolein gas at an outlet portion of the reactor.

Comparative Example 1

An operation was performed by using same catalyst and reaction apparatus as in Example except that stainless steel-made containers (rectifier 1 and rectifier 2) which had been provided in an outlet retention portion in Example were removed.

After the operation was performed for one month, since a temperature of the outlet portion of the reactor was rapidly increased by a decomposition reaction of an acrolein gas, the operation was stopped.

While the present invention has been described in detail and with reference to specific embodiments thereof, it will be apparent to one skilled in the art that various changes and modifications can be made therein without departing from the spirit and scope thereof.

This application is based on Japanese patent application (Patent Application No. 2004-143305) filed on May 13, 2004, the entire contents thereof being hereby incorporated by reference.

INDUSTRIAL APPLICABILITY

According to a method according to the present invention, an operation can continuously be performed without causing decomposition of (meth)acrolein. Therefore, (meth)acrolein or (meth)acrylic acid can be produced with high purity.

The invention claimed is:

1. A production method for (meth)acrolein or (meth)acrylic acid, in which (meth)acrolein or (meth) acrylic acid is obtained by performing a catalytic gas phase oxidation reaction on propylene, propane or isobutylene by using a molecular oxygen by means of a heat-exchange type multi-tubular reactor, comprising a tube bundle portion in which a multiple of reaction tubes each filled with a catalyst are aligned in parallel to one another and a tube plate which is adjacent to a downstream side of the tube bundle portion of the reaction tubes and forms a lead-out portion for a reaction gas, in which the tube bundle portion of the reaction tubes has a hollow columnar constitution as a whole, being characterized in that a rectifier is provided on a tube plate.

2. The production method for (meth)acrolein or (meth)acrylic acid as claimed in claim 1, being characterized in that the rectifier is provided in a central portion of the tube plate.

3. The production method for (meth)acrolein or (meth)acrylic acid as claimed in claim 1, being characterized in that the rectifier is provided in a peripheral portion of the tube plate.

4. The production method for (meth)acrolein or (meth)acrylic acid as claimed in claim 1, being characterized in that the rectifier is provided in each of a central portion and a peripheral portion of the tube plate.

* * * * *